(12) United States Patent
Maskara et al.

(10) Patent No.: US 8,731,667 B2
(45) Date of Patent: May 20, 2014

(54) PACING OUTPUT CONFIGURATION SELECTION FOR CARDIAC RESYNCHRONIZATION THERAPY PATIENTS

(75) Inventors: Barun Maskara, Blaine, MN (US); Yinghong Yu, Shoreview, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 361 days.

(21) Appl. No.: 13/017,475

(22) Filed: Jan. 31, 2011

(65) Prior Publication Data

US 2011/0130801 A1 Jun. 2, 2011

Related U.S. Application Data

(62) Division of application No. 11/654,938, filed on Jan. 18, 2007, now Pat. No. 7,890,172.

(51) Int. Cl.
*A61N 1/365* (2006.01)

(52) U.S. Cl.
USPC .......................................... 607/25

(58) Field of Classification Search
USPC .................................... 607/17, 25
See application file for complete search history.

(56) References Cited

U.S. PATENT DOCUMENTS

| | | | |
|---|---|---|---|
| 5,235,976 A | 8/1993 | Spinelli | |
| 5,954,753 A | 9/1999 | Alt | |
| 6,766,189 B2 | 7/2004 | Yu et al. | |
| 6,792,308 B2 | 9/2004 | Corbucci | |
| 6,804,555 B2 | 10/2004 | Warkentin | |
| 6,993,389 B2 | 1/2006 | Ding | |
| 7,065,405 B2 | 6/2006 | Pastore et al. | |
| 7,110,817 B2 | 9/2006 | Yu et al. | |
| 7,123,960 B2 | 10/2006 | Ding | |
| 7,142,922 B2 | 11/2006 | Spinelli | |
| 2004/0098056 A1 | 5/2004 | Ding et al. | |
| 2004/0102812 A1 | 5/2004 | Yonce et al. | |
| 2004/0122479 A1 | 6/2004 | Spinelli et al. | |
| 2004/0215249 A1* | 10/2004 | Corbucci | 607/9 |
| 2006/0041279 A1 | 2/2006 | Yu et al. | |
| 2006/0116727 A1 | 6/2006 | Ding | |
| 2006/0149326 A1 | 7/2006 | Prinzen et al. | |
| 2006/0167510 A1 | 7/2006 | Rouw | |
| 2006/0224198 A1 | 10/2006 | Dong et al. | |
| 2006/0247692 A1 | 11/2006 | Yang et al. | |

OTHER PUBLICATIONS

File History for U.S. Appl. No. 11/654,938.

(Continued)

*Primary Examiner* — Tammie K Heller
(74) *Attorney, Agent, or Firm* — Brooks, Cameron & Huebsch, PLLC

(57) ABSTRACT

Cardiac therapy systems include multiple electrodes respectively positionable at multiple left ventricular electrode sites. A pulse generator is coupled to the electrodes and configured to deliver a cardiac resynchronization therapy (CRT). A processor is configured to measure, for each left ventricular electrode site, a timing interval between first and second cardiac signal features associated with left ventricular depolarization. The timing interval is associated with a degree of responsiveness of each left ventricular electrode site to CRT. The processor is configured to determine a pacing output configuration that provides improved patient responsiveness to CRT based on the timing interval measurements and to select at least one left ventricular electrode site from the plurality of left ventricular electrode sites based on the timing interval measurements. The processor may be configured to monitor for a change in hemodynamic status of the patient based on a change in the timing interval.

20 Claims, 8 Drawing Sheets

(56) References Cited

OTHER PUBLICATIONS

Medtronic, "The "Long and Short" of Predicting CRT Response by QRS Duration", NewsRhythms, Feb. 4, 2004.

Waggoner et al., "Improvements in Left Ventricular Diastolic Function after Cardiac Resynchronization Therapy are Coupled to Response in Systolic Performance", Journal of the American College of Cardiology, vol. 46, No. 12, 2005.

Aranda, "Management of the Nonresponder", 2005 Annual Scientific Meeting, 2005.

Bax et al., "How to Predcit Response to Cardiac Resynchronization Therapy?", European Heart Journal, Mar. 24, 2005.

* cited by examiner

PACING OUTPUT CONFIGURATION SELECTION FOR CARDIAC RESYNCHRONIZATION THERAPY PATIENTS

RELATED APPLICATIONS

This application is a division of U.S. patent application Ser. No. 11/654,938 filed on Jan. 18, 2007, now U.S. Pat. No. 7,890,172, to which Applicant claims priority under 35 U.S.C. §120, and which is incorporated herein by reference.

FIELD OF THE DISCLOSURE

The present invention relates generally to cardiac pacing devices and therapies, and more specifically, to systems and methods for selecting a pacing output configuration that improves a patient's responsiveness to cardiac resynchronization therapy.

BACKGROUND

When functioning normally, the heart produces rhythmic contractions and is capable of pumping blood throughout the body. The heart has specialized conduction pathways in both the atria and the ventricles that enable the rapid conduction of excitation impulses (i.e. depolarizations) from the SA node throughout the myocardium. These specialized conduction pathways conduct the depolarizations from the SA node to the atrial myocardium, to the atrio-ventricular node, and to the ventricular myocardium to produce a coordinated contraction of both atria and both ventricles.

The conduction pathways synchronize the contractions of the muscle fibers of each chamber as well as the contraction of each atrium or ventricle with the opposite atrium or ventricle. Without the synchronization afforded by the normally functioning specialized conduction pathways, the heart's pumping efficiency is greatly diminished. Patients who exhibit pathology of these conduction pathways can suffer compromised cardiac output.

Normally, the muscular walls of each chamber of the heart contract synchronously in a precise sequence to efficiently circulate blood through the heart. In particular, both the right and left atriums contract (e.g., atrial contractions) and relax synchronously. Shortly after the atrial contractions, both the right and left ventricles contract (e.g., ventricular contractions) and relax synchronously. Several disorders or arrhythmias of the heart can prevent the heart from operating normally, such as, blockage of the conduction system, heart disease (e.g., coronary artery disease), abnormal heart valve function, or heart failure.

Blockage in the conduction system can cause a slight or severe delay in the electrical impulses propagating through the atrioventricular node, causing inadequate ventricular contractions and filling. In situations where the blockage is in the ventricles (e.g., the right and left bundle branches), the right and/or left ventricles can only be excited through slow muscle tissue conduction. As a result, the muscular walls of the affected ventricle do not contract synchronously (e.g., asynchronous contraction), thereby, reducing the overall effectiveness of the heart to pump oxygen-rich blood throughout the body.

Cardiac rhythm management devices have been developed that provide pacing stimulation to one or more heart chambers in an attempt to improve the rhythm and coordination of atrial and/or ventricular contractions. Cardiac rhythm management devices typically include circuitry to sense signals from the heart and a pulse generator for providing electrical stimulation to the heart. Leads extending into the patient's heart chamber and/or into veins of the heart are coupled to electrodes that sense the heart's electrical signals and deliver electrical stimulation to the heart in accordance with various therapies for treating cardiac arrhythmias.

Pacemakers are cardiac rhythm management devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

Pacing therapy has been used in the treatment of heart failure (HF). Heart failure causes diminished pumping power of the heart, resulting in the inability to deliver enough blood to meet the demands of peripheral tissues. Heart failure may affect the left heart, right heart or both sides of the heart, and may cause weakness, loss of breath, and build up of fluids in the lungs and other body tissues. For example, HF may occur when deterioration of the muscles of the heart produce an enlargement of the heart and/or reduced contractility. The reduced contractility decreases the cardiac output of blood and may result in an increased heart rate. In some cases, HF is caused by unsynchronized contractions of the left and right heart chambers, denoted atrial or ventricular dysynchrony. Particularly when the left or right ventricles are affected, the unsynchronized contractions can significantly decrease the pumping efficiency of the heart.

Pacing therapy to promote synchronization of heart chamber contractions to improve cardiac function is generally referred to as cardiac resynchronization therapy (CRT). Some cardiac pacemakers are capable of delivering CRT by pacing multiple heart chambers. Pacing pulses are delivered to the heart chambers in a sequence that causes the heart chambers to contract in synchrony, increasing the pumping power of the heart and delivering more blood to the peripheral tissues of the body. In the case of dysynchrony of right and left ventricular contractions, a biventricular pacing therapy may pace one or both ventricles. Bi-atrial pacing or pacing of all four heart chambers may alternatively be used.

SUMMARY

The present invention is directed to systems and methods for selecting a pacing output configuration that improves a patient's responsiveness to cardiac resynchronization therapy (CRT). Embodiments of the present invention are directed to cardiac therapy systems that include multiple electrodes respectively positionable at multiple locations within at least a left ventricle for sensing cardiac electrical signals from a plurality of left ventricular electrode sites. A pulse generator is coupled to the multiple electrodes and configured to deliver at least a CRT.

A processor is coupled to the multiple electrodes and the pulse generator. The processor is configured to measure, for each left ventricular electrode site, a timing interval between first and second cardiac signal features associated with left ventricular depolarization. The timing interval is preferably associated with a degree of responsiveness of each left ventricular electrode site to CRT. The processor is configured to determine a pacing output configuration that provides improved patient responsiveness to CRT based on the timing interval measurements and to select at least one left ventricular electrode site from the plurality of left ventricular electrode sites based on the timing interval measurements.

In accordance with other embodiments, cardiac therapy systems of the present invention may be configured to include multiple electrodes respectively positionable at multiple locations within at least a left ventricle for sensing cardiac electrical signals from at least one left ventricular electrode site, and a pulse generator coupled to the multiple electrodes and configured to deliver at least a CRT. A processor is coupled to the multiple electrodes and the pulse generator. The processor is configured to detect a change in a timing interval between first and second cardiac signal features associated with ventricular depolarization, the timing interval associated with a degree of responsiveness of the at least one left ventricular electrode site to CRT. The processor is configured to monitor for a change in hemodynamic status of the patient based on the detected timing interval change.

According to further embodiments, methods of the present invention may be implemented that involve sensing of cardiac electrical signals from a plurality of left ventricular electrode sites, and measuring, for each left ventricular electrode site, a timing interval between first and second cardiac signal features associated with left ventricular depolarization. The timing interval is preferably associated with a degree of responsiveness of each left ventricular electrode site to CRT. A pacing output configuration is determined that provides improved patient responsiveness to CRT based on the timing interval measurements. Determining the pacing output configuration may include selecting at least one left ventricular electrode site from the plurality of left ventricular electrode sites based on the timing interval measurements.

In accordance with other embodiments, methods of the present invention may be implemented that involve sensing, from within a patient, one or more cardiac electrical signals, including a cardiac electrical signal from at least one left ventricular electrode site. A change in a timing interval between first and second cardiac electrical signal features associated with ventricular depolarization may be detected, the timing interval associated with a degree of responsiveness of the at least one left ventricular electrode site to a CRT. Methods may further involve monitoring for a change in hemodynamic status of the patient based on the detected timing interval change.

Figure 1:
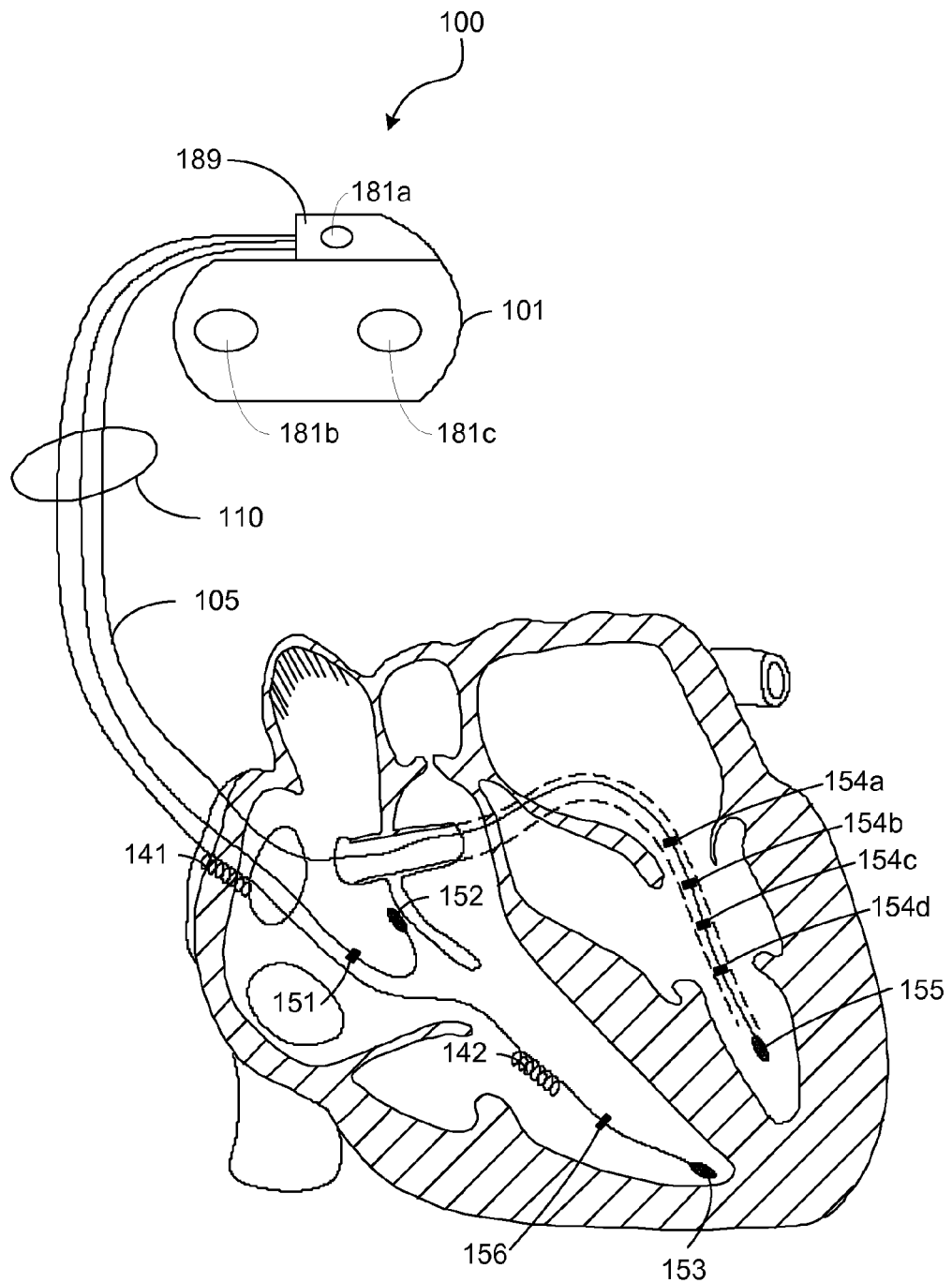
FIG. 1 illustrates a patient-implantable therapy device that may be configured to implement a pacing output configuration selection methodology in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described hereinbelow. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

A cardiac therapy device implemented in accordance with the present invention may deliver electrical stimulation pulses to one or more electrodes disposed within a heart chamber and/or otherwise electrically coupled to the myocardium to initiate contractions of the chamber. Embodiments of the invention are directed to systems and methods for selecting a pacing output configuration that improves a patient's responsiveness to cardiac resynchronization therapy. Embodiments of the invention are directed to systems and methods for measuring, for each of a number of different electrode sites, a timing interval between specified cardiac signal features associated with left ventricular depolarization, where the timing interval is reflective of a degree of responsiveness of each electrode site to CRT. Based on the timing intervals associated with the electrode sites, a pacing output configuration is determined, which preferably includes a least a pacing site selected from the various electrode sites or a pacing vector associated with the selected pacing site. The pacing output configuration may also include selection of one or more pacing parameters, such as AV delay, based on pacing site selection.

Electrode site selection is preferably based on timing interval measurements associated with ventricular depolarization. These timing interval measurements may be used to identify and/or select electrode sites(s) that provide for improved responsiveness to cardiac resynchronization therapy. Changes in such measured timing intervals may be monitored to evaluate changes in a patient's hemodynamic status, generate warnings in response to measurements that change beyond a threshold, and/or to modify electrode site selection and/or a pacing parameter (e.g., AV delay) to improve patient responsiveness to CRT and the patient's hemodynamic status.

According to various embodiments, electrode sites may be evaluated to identify those that will respond to CRT (referred to herein as "responder sites"), and such identified responder sites may be further evaluated to determine their relative degree of responsiveness to CRT. Responder sites may be characterized by late activation of depolarization and/or prolonged depolarization. Electrode site characterization may be implemented through analysis of a timing interval (e.g., Q1-LV or Q-LV) defined between a first deflection (e.g., Q1 or Q) and a maximum deflection (e.g., LV) of a ventricular depolarization for a given electrode site. The Q1-LV timing interval refers to a timing interval defined between the start of a QRS deflection of the LV electrogram and the peak of the QRS deflection of the LV electrogram. The Q-LV timing interval refers to a timing interval defined between the start of a QRS deflection of a surface ECG and the peak of the QRS deflection of the LV electrogram.

A relationship exists between the intrinsic depolarization interval (e.g., Q1-LV or Q-LV) and the increase in peak rate of increase of left ventricle pressure (LV dp/dt) due to CRT, both of which are associated with greater cardiac output. Intervals associated with various cardiac electrode sites can be compared, preferably by an implantable therapy device or a patient-external processor, to determine the most effective and/or efficient pacing output configuration. Such comparisons may be repeated over time to determine if changes to the pacing output configuration can be made that will improve patient responsiveness to CRT. Changes to the pacing output configuration may include a change to one or more of the pacing electrode site(s), pacing vector(s), and pacing parameter(s), such as AV delay.

The patient's Q1-LV or Q-LV timing interval may be monitored and tracked, such as by the therapy device and/or by a programmer or advanced patient management system. Changes in the patient's Q1-LV or Q-LV timing interval relative to a threshold may be used to detect an adverse change in the patient's hemodynamic status. Changes in the patient's Q1-LV or Q-LV timing interval may also be monitored to track the progression or regression of a patient's heart failure status.

If the patient's Q1-LV or Q-LV timing interval falls below a threshold, a clinician alert may be generated. A change in this timing interval relative to a threshold may trigger a re-optimization procedure, whereby available electrode sites/vectors are re-evaluated to determine if an alternative electrode site having a greater intrinsic depolarization timing interval than that associated with a current pacing output configuration is available. If so, the therapy device may be programmed to automatically select a pacing output configuration that includes the alternative electrode site. A pacing parameter, such as AV delay, may also be adjusted in response to selection of the alternative electrode site. Alternatively, a physician may be notified that a change in pacing output configuration is needed or desired. The physician may then modify the pacing output configuration accordingly, such as by use of a programmer of advanced patient management system.

Turning now to FIG. 1, there is shown a therapy device 100 that represents one of several possible embodiments of a patient-implantable device that may be used in conjunction with pacing output configuration determinations made in accordance with the present invention. The therapy device 100 includes cardiac rhythm management (CRM) circuitry enclosed within an implantable housing 101. The CRM circuitry is electrically coupled to an intracardiac lead system 110.

Portions of the intracardiac lead system 110 are shown inserted into the patient's heart. The lead system 110 includes cardiac pace/sense electrodes 151-156 positioned in, on, or about one or more heart chambers for sensing electrical signals from the patient's heart and/or delivering pacing pulses to the heart. The intracardiac sense/pace electrodes 151-156, such as those illustrated in FIG. 1, may be used to sense and/or pace one or more chambers of the heart, including the left ventricle, the right ventricle, the left atrium and/or the right atrium. The lead system 110 is shown to include one or more defibrillation electrodes 141, 142 for delivering defibrillation/cardioversion shocks to the heart.

The left ventricular lead 105 incorporates multiple electrodes 154a-154d positioned at various locations within, on or about the left ventricle. Stimulating the ventricle at multiple locations or at a single selected location may provide for increased cardiac output in a patients suffering from HF. In accordance with various embodiments described herein, one or more of the electrodes 154a-154d are selected for pacing the left ventricle. In other embodiments, leads having multiple pacing electrodes positioned at multiple locations within a chamber, such as the one illustrated by the left ventricular lead 105 of FIG. 1, may be implanted within any or all of the heart chambers. One or more electrodes positioned within one or more chambers may be selected based on timing interval measurements as described herein. Electrical stimulation pulses may be delivered to the chambers via the selected electrodes according to a timing sequence and output configuration that enhances cardiac function.

Portions of the housing 101 of the implantable device 100 may optionally serve as one or multiple can or indifferent electrodes. The housing 101 is illustrated as incorporating a header 189 that may be configured to facilitate removable attachment between one or more leads and the housing 101. The housing 101 of the therapy device 100 may include one or more can electrodes 181b, 181c. The header 189 of the therapy device 100 may include one or more indifferent electrodes 181a. The housing 101 and/or header 189 may include any number of electrodes positioned anywhere in or on the housing 101 and/or header 189.

The cardiac electrodes and/or other sensors disposed within or on the housing 101 or lead system 110 of the therapy device 100 may produce signals used for detection and/or measurement of various physiological parameters, such as transthoracic impedance, respiration rate, minute ventilation, heart rate, cardiac dysynchrony, activity, posture, blood chemistry, O2 saturation, heart sounds, wall stress, wall strain, hypertrophy, inter-electrode impedance, electrical delays (PR interval, AV interval, QRS width, etc.), activity, cardiac chamber pressure (e.g., left ventricular pressure), cardiac output, temperature, heart rate variability, depolarization amplitudes, depolarization timing, and/or other physiological parameters.

For example, in some configurations, the implantable device 100 may incorporate one or more transthoracic impedance sensors that may be used to acquire the patient's respiratory waveform, and/or to acquire other respiratory-related information. The transthoracic impedance sensor may include, for example, one or more intracardiac electrodes 141, 142, 151-156 positioned in one or more chambers of the heart. The intracardiac electrodes 141, 142, 151-156 may be coupled to impedance drive/sense circuitry positioned within the housing 101 of the therapy device 100. Information from the transthoracic impedance sensor may be used to adapt the rate of pacing to correspond to the patient's activity or metabolic need.

Communications circuitry is disposed within the housing 101 for facilitating communication between the CRM circuitry and a patient-external device, such as an external programmer or advanced patient management (APM) system. The communications circuitry may also facilitate unidirectional or bidirectional communication with one or more implanted, external, cutaneous, or subcutaneous physiologic or non-physiologic sensors, patient-input devices and/or information systems.

In certain embodiments, the therapy device 100 may include circuitry for detecting and treating cardiac tachyarrhythmia via defibrillation therapy and/or anti-tachyarrhythmia pacing (ATP). Configurations providing defibrillation capability may make use of defibrillation coils 141, 142 for delivering high energy shocks to the heart to terminate or mitigate tachyarrhythmia. It is understood that defibrillation coils 141, 142 are employed in therapy devices 100 that provide for both pacing and cardioversion/defibrillation functionality.

In some embodiments, the implantable therapy device 100 may include circuitry for selection of pacing electrode(s), electrode sites, timing/delay sequences and/or pacing output configuration to be applied via one or more electrodes. In other embodiments, the therapy device 100 may diagnose a change in a patient's hemodynamic status based on timing interval measurements derived from signals sensed from one or more electrodes, such as electrodes 154A-D, or from signals derived from one or more hemodynamic sensors, such as a pressure sensor.

In other embodiments, the implantable therapy device 100 may transfer sensed or derived information relevant to pacing output configuration or diagnosis to a patient-external device. Following download of the implantably sensed or derived information, selection of the pacing output configuration or a diagnosis of hemodynamic status may be made by the patient-external device or may be made by a clinician using information provided via the patient-external device.

Pacing output configuration involves selection of the site or sites of pacing within a heart chamber and/or temporal sequence of the pacing pulses delivered to the multiple sites, and may also optionally involve selection of particular pulse characteristics (e.g., amplitude, duration, anodal/cathodal polarity, AV interval, and waveshape) used for the pacing pulses. Selection of the pacing output configuration is particularly desirable for optimal application of cardiac resynchronization therapy.

Heart failure, long term pacing, ischemia, myocardial infarction and/or other factors can produce non-uniformities in the electrical, mechanical or electromechanical properties of the myocardium. These non-uniformities can cause a heart chamber to contract in an uncoordinated manner resulting in inefficient pumping action. The location of the pacing site or sites and/or other properties of the pacing output configuration affects the spread of the depolarization excitation which in part determines the manner in which the chamber contracts. In a pacemaker equipped with multiple pacing electrodes respectively disposed at multiple pacing sites within a heart chamber, the ability to select between one or more electrodes, temporal sequence, and/or pulse waveform characteristics for delivery of pacing can be used enhance the contractile function of the heart chamber.

Multi-site pacemakers, such as illustrated herein, are capable of delivering pacing pulses to multiple sites of the atria and/or ventricles during a cardiac cycle. Certain patients may benefit from activation of parts of a heart chamber, such as a ventricle, at different times in order to distribute the pumping load and/or depolarization sequence to different areas of the ventricle. A multi-site pacemaker has the capability of switching the output of pacing pulses between selected electrodes or groups of electrodes within a heart chamber during different cardiac cycles. For example, the pacing pulses may be delivered to the heart chamber at specified locations and at specified times during the cardiac cycle to enhance the synchrony of the contraction. Amplitude, pulse duration, anodal/cathodal polarity and/or waveshape of the pacing pulses may also be altered to enhance pumping function.

Various abnormalities of the heart can change the pumping efficiency of the heart. Various arrhythmias include an abnormally fast heart rate (e.g., tachycardia), an abnormally slow heart rate (e.g., bradycardia), or a normal rate but where the depolarization is abnormally propagated (e.g., ectopic, or conduction system defect). The existence of an arrhythmia typically indicates that the heart's rhythm initiation and/or conduction system is functioning abnormally. Cardiac resynchronization therapy can be used, among other applications, to treat abnormal electrical conduction.

In particular, CRT can be used to deliver electrical stimulation to portions of the heart to resynchronize the heart's activation, thereby, improving the efficiency of atrial and ventricular contractions necessary to circulate blood throughout the body. The amount of benefit derived from CRT, however, typically varies depending upon the severity of the abnormality of the heart's conduction system. Therefore, prior to cardiac electrode placement or cardiac electrode output configuration, it is preferable to evaluate whether the heart's conduction system is normal or abnormal and whether stimulation will improve cardiac output.

Not all possible cardiac electrode sites in the ventricles are ideal for effective cardiac pacing. For example, various cardiac electrode sites of a particular patient's left ventricle may not significantly improve overall cardiac output when paced. Other cardiac electrode sites may significantly improve overall cardiac output when paced. Cardiac electrode sites that sufficiently improve the overall cardiac output when paced are called responder sites. Cardiac electrode sites that do not sufficiently improve the overall cardiac output when paced are called non-responder sites.

In various embodiments of the present invention, a pacing output configuration for delivering CRT by an implantable cardiac therapy device is selected and/or modified based on timing interval measurements derived from a number of such responder sites, initially during implant and thereafter during post-implant CRT delivery. Monitoring such timing interval measurements over time allows for tracking of changes in patient responsiveness to CRT, changes in patient hemodynamic status, and, if needed, re-optimization of selected electrode/responder sites.

Responder sites can be characterized by late activation of depolarization and/or prolonged depolarization. These can be assessed through analysis of the interval (Q1-LV or Q-LV) from the first deflection (Q1 or Q) to the maximum deflection (LV) at the stimulation site of the ventricular depolarization, as is discussed in greater detail in commonly owned U.S. Pat. Nos. 5,235,976, 6,993,389, and 7,142,922 which are hereby incorporated herein by reference.

As was discussed previously, a relationship exists between the intrinsic depolarization interval (e.g., Q1-LV or Q-LV) and the increase in peak rate of increase of left ventricle pressure (LV dp/dt) due to CRT, both of which are associated with greater cardiac output. Intervals associated with various cardiac electrode sites can be compared, preferably by an implantable therapy device or a patient-external processor, to determine the most effective and/or efficient pacing output configuration. Such comparisons may be repeated over time to determine if changes to the pacing output configuration can be made that will improve patient responsiveness to CRT. Changes to the pacing output configuration may include a change to one or more of the pacing electrode site(s), pacing vector(s), and pacing parameter(s), such as AV delay.

Identification and prioritization of stimulation sites that may have a positive response to CRT can be performed using the intervals described above, where at least the maximum deflection point (LV) is preferably measured from an intracardiac electrogram. For example, if the timing interval (Q1-LV or Q-LV) for a particular electrode site is greater than an equivalent timing interval for other electrode sites, then the particular electrode site may be considered a higher priority when considering whether, and in what configuration, to deliver CRT to the electrode sites.

Embodiments of the invention are directed to methods for configuring the pacing output configuration of a cardiac therapy device by evaluating an interval of a sensed signal for a particular cardiac electrode site, the interval defined between a first deflection to a maximum deflection of depolarization of a ventricle. The duration of this interval, which is typically compared to a threshold, indicates whether or not the cardiac electrode site will respond to CRT. A typical threshold associated with the Q1-LV timing interval is about 100 ms. A typical threshold associated with the Q-LV timing interval is about 80 ms. Methods of the present invention may also involve comparing the timing interval to other sensed intervals for various cardiac electrode sites and configuring the cardiac pacing output configuration, such as electrode site/vector selection and pacing parameter (e.g., AV delay) adjustment, based on the comparison.

Figure 2:
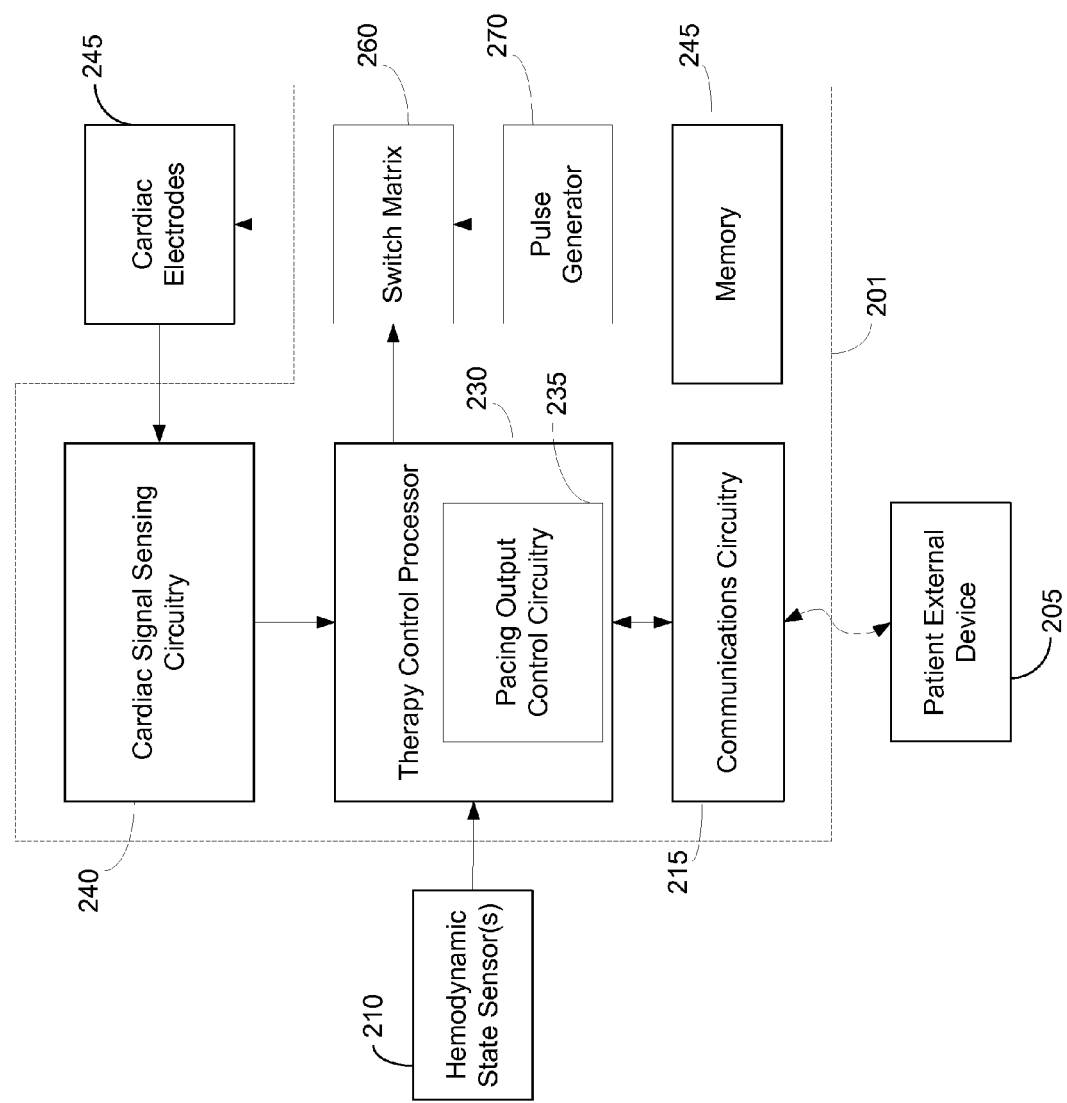
FIG. 2 is a block diagram of circuitry used to select a pacing output configuration in accordance with embodiments of the invention.

FIG. 2 is a block diagram of circuitry used for establishing and adjusting the pacing output configuration of a cardiac therapy device in accordance with embodiments of the present invention. Multiple cardiac electrodes 245 are disposed at multiple locations within or on a heart chamber, such as in a manner previously discussed. Intrinsic cardiac signals, such as signals associated with ventricular depolarization, may be collected by cardiac electrodes 245 and then received by the cardiac signal sensing circuitry 240.

One or more sensors 210 are configured to sense physiological factors indicative of a patient's hemodynamic status. The sensors 210 may be implantable, cutaneous or other type of sensor. For example, one or more sensors 210 may be disposed within or on the housing or lead system of the therapy device and produce signals used for detection and/or measurement of various physiological parameters indicative of a patient's hemodynamic status. Such sensors 210 and/or cardiac electrodes 245 may be configured, for example, to sense transthoracic impedance, respiration rate, minute ventilation, heart rate, cardiac dysynchrony, activity, posture, blood chemistry, O2 saturation, heart sounds, wall stress, wall strain, hypertrophy, inter-electrode impedance, electrical delays (PR interval, AV interval, QRS width, etc.), activity, cardiac chamber pressure, cardiac output, temperature, heart rate variability, depolarization amplitudes, depolarization timing, and/or other physiological parameters.

According to one approach, a detected change in hemodynamic status of the patient may trigger a check to determine if a change in the pacing output configuration would be beneficial. In various implementations, one or more of the hemodynamic status sensors 210 used to trigger re-evaluation of the pacing output configuration may be selectable by the therapy device or by a clinician, such as by way of an APM system interface. The hemodynamic status sensor(s) 210 may also be used to monitor changes in the patient's hemodynamic status to verify that changes to the pacing output configuration improve the patient's responsiveness to CRT.

The therapy control processor 230, for example, may be configured to assess CRT responsiveness for each of a number of electrode sites. For example, the therapy control processor 230, in conjunction with the cardiac electrodes 245, may assess a parameter associated with a degree of responsiveness of a left ventricular electrode site to cardiac resynchronization. Such parameters may include depolarization characteristics such as depolarization delays (e.g., Q1-LV or Q-LV interval), atrioventricular timing intervals, depolarization amplitude, depolarization-repolarization intervals, depolarization thresholds, and/or other depolarization characteristics. The therapy control processor 230 may be configured to identify features of a sensed signal corresponding to an atrial and/or ventricular depolarization/repolarization. Such features may include the start of ventricular depolarization, a peak initial deflection corresponding to ventricular depolarization, and a maximum deflection associated with ventricular depolarization, among other features.

In one embodiment, depolarization timing intervals may be measured at each electrode site during an intrinsic systolic contraction. A distribution of the depolarization timing intervals can be determined by measuring the time interval between the start of ventricular depolarization and a maximum signal deflection associated with ventricular depolarization detected via cardiac electrograms sensed at each of the cardiac electrodes during the contraction.

In accordance with some embodiments, cardiac sensing circuitry 240 may include individual sense amplifiers and peak detectors for each electrode in the ventricle. In other embodiments, a bipolar sensing technique may be used to reduce the number of sense amplifiers and/or other signal processing circuitry required to detect the depolarization delay distribution. Measurement of the distribution of depolarization timing intervals in a heart chamber may be accomplished using the techniques described in commonly owned U.S. Pat. No. 7,239,913 or 7,697,977, which are incorporated herein by reference.

After measurement of the parameter associated with a degree of responsiveness of an electrode site to CRT, pacing output control circuitry 235 selects an appropriate pacing output configuration. According to one aspect, the pacing output control circuitry 235 may select an electrode corresponding to a pacing site having a longest depolarization timing interval or may select a number of electrodes for pacing in a pattern or sequence based on their respective depolarization timing intervals. In some configurations, the electrode associated with the longest depolarization timing interval may be paced first, the electrode associated with the second longest interval may be paced next, and so forth.

As described above, one way of selecting a pacing site for resynchronization therapy is to measure the depolarization delays of a number of potential pacing sites. One or more sites that are demonstrated to be excited later in the contraction sequence may then be selected as pacing sites. Pacing the latest activated site or pacing multiple sites in a sequence corresponding to their respective timing intervals may provide for a more coordinated contraction profile.

The embodiment illustrated in FIG. 2 also includes a switch matrix 260. The switch matrix 260 can arrange the pacing pulses delivered through the various electrodes 245 as directed by the pacing output control circuitry 235. The switch matrix 260 can also receive pacing pulses from pulse generator 270 and route the pacing pulses to the appropriate cardiac electrodes 245 as directed by the pacing output control circuitry 235.

Circuitry for assessing CRT responsiveness of a number of electrode sites and determining an appropriate pacing output configuration may be provided in the therapy device 201. In one embodiment, the components/processes included within the dashed line 201 of FIG. 2 may be provided by an implantable therapy device such as that illustrated in FIG. 1. Such a device may include a power supply (not shown) and memory 245 for storing program instructions and/or data. In various configurations, the memory 245 may be used to store information associated with CRT responsiveness assessment, change in hemodynamic condition, and/or present and past pacing output configurations. The information stored in the memory 245 may be used to create a lookup table for future reference that may be used to facilitate selection of a beneficial pacing output configuration. In addition, the stored information may be used to provide a log of events for display or analysis at a later time. The therapy device 201 also includes communications circuitry 215 for communicating with a patient-external device 205, such as a programmer or advanced patient management system.

In some configurations, the implantable device may provide some of the functionality for selection of pacing output configuration, and a patient-external device may provide some of the functionality. For example, in one embodiment, the patient-external device communicates with the implantable device over a telemetry link and receives either raw data, markers corresponding to particular sensed events, and/or measurements of timing intervals or other signal characteristics as determined by the implantable device. The external device may then generate CRT responsiveness data and compute optimal settings for the pacing output configuration which are either transmitted to the implantable device for immediate reprogramming, or presented to a clinician operating the external device as a recommendation. Alternatively, the external device may present the raw data, markers and/or measurements to the clinician who may then program the implantable device in accordance with an algorithm.

Figure 3:
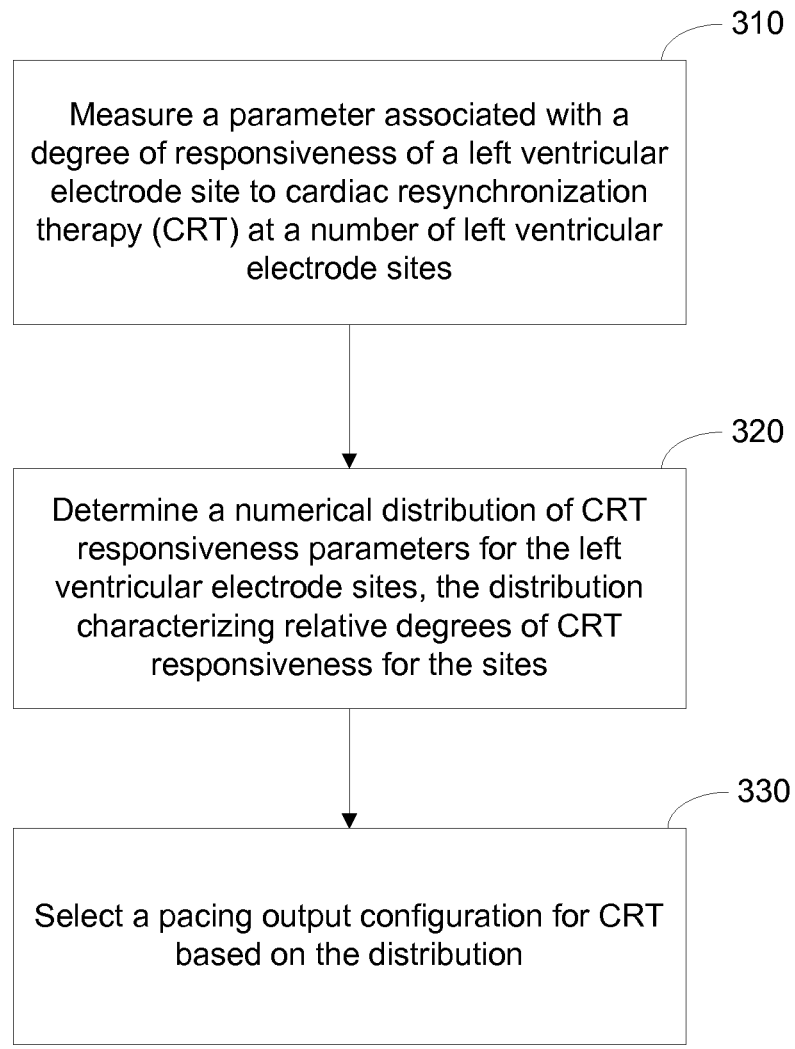
FIG. 3 is a flow diagram illustrating a process for selecting a pacing output configuration in accordance with embodiments of the invention.

FIG. 3 is a flow graph illustrating an approach for selecting the pacing output configuration of a therapy device to improve a patient's responsiveness to CRT in accordance with one embodiment of the present invention. In this illustrative example, optimization of the pacing output configuration is based on a numerical distribution of CRT responsiveness of left ventricular electrode sites. According to one approach, a parameter associated with a degree of responsiveness of a left ventricular electrode site to CRT is measured 310 at a number of left ventricular electrode sites. The parameter can include various timing intervals of left ventricular depolarization as discussed herein.

Once parameters are measured for the left ventricular electrode sites, a numerical distribution of CRT responsiveness for the left ventricular electrode sites is determined 320, the distribution characterizing relative degrees of CRT responsiveness. The distribution may be organized in various ways, depending on the nature of the parameter and the measurement. In an embodiment in which the parameter is a timing interval associated with ventricular depolarization, the distribution may be organized according to the various lengths of the timing interval measured. The numerical distribution may then be used to select 330 a pacing output configuration for CRT. Pacing sites with greater responsiveness to CRT, according to the distribution, may be more likely to receive pacing stimulation than pacing sites with relatively less responsiveness to CRT.

Figure 4:
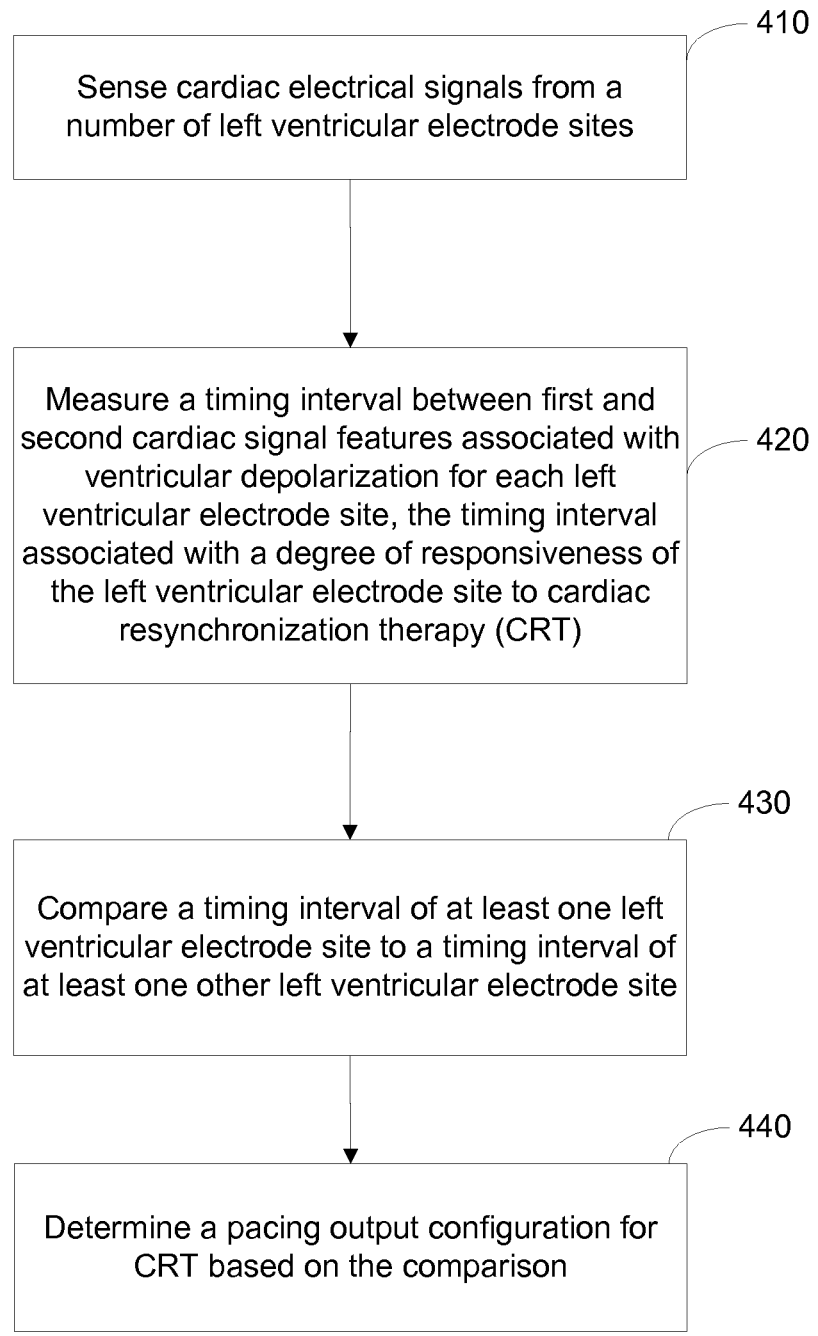
FIG. 4 is a flow diagram illustrating another process for determining a pacing output configuration in accordance with embodiments of the invention.

FIG. 4 is a flow graph illustrating an approach for selecting a pacing output configuration of a therapy device to improve a patient's responsiveness to CRT in accordance with another embodiment of the present invention. In this illustrative example, optimization of the pacing output configuration is based on a comparison of timing intervals associated with ventricular depolarization at a number of left ventricular electrode sites. According to one approach, cardiac electrode signals for a number of left ventricular electrode sites are sensed 410. After the left ventricular cardiac electrode signals are sensed, each from a left ventricular electrode site, a timing interval between first and second cardiac signal features associated with ventricular depolarization is measured 420 for each left ventricular electrode site, where the timing interval is associated with a degree of responsiveness of the left ventricular electrode site to CRT.

For example, a timing interval of a sensed left ventricular depolarization may be measured. The timing interval may be measured by calculating the time between when a first feature of an electrogram (EGM) or electrocardiogram (ECG) signal associated with left ventricular depolarization is sensed and a second feature of an EGM or ECG signal associated with left ventricular depolarization is sensed. The first feature may be the peak of a first deflection of ventricular depolarization and the second feature may be the maximum deflection of ventricular depolarization. By way of example, the first feature may be the first deflection of left ventricular depolarization represented by Q1 or Q, and the second feature may be the maximum deflection of ventricular depolarization, represented by LV. The process of measuring time intervals according to block 420 is repeated for each of the left ventricular electrode sites. As discussed herein, the timing interval for each electrode site may be indicative of a degree of responsiveness of the electrode site to CRT.

After timing intervals are measured for the left ventricular electrode sites, at least one left ventricular electrode site timing interval is compared 430 to a timing interval of at least one other left ventricular electrode site. Preferably, the measured timing intervals are compared to one another so as to determine the timing interval of greatest duration. The comparison may be done in various ways, depending on the nature of the timing interval and the measurement.

The comparison 430 may then be used to determine 440 a pacing output configuration for CRT. Pacing sites with greater responsiveness to CRT, according to the comparison, may be more likely to receive pacing stimulation than pacing sites with relatively less responsiveness to CRT. If the comparison is made according to the length of a time interval, then the electrode site with the longest time interval may have priority in the pacing output configuration and, as such, may be more likely to receive pacing stimulation or receive pacing stimulation before other electrode sites.

Figure 5:
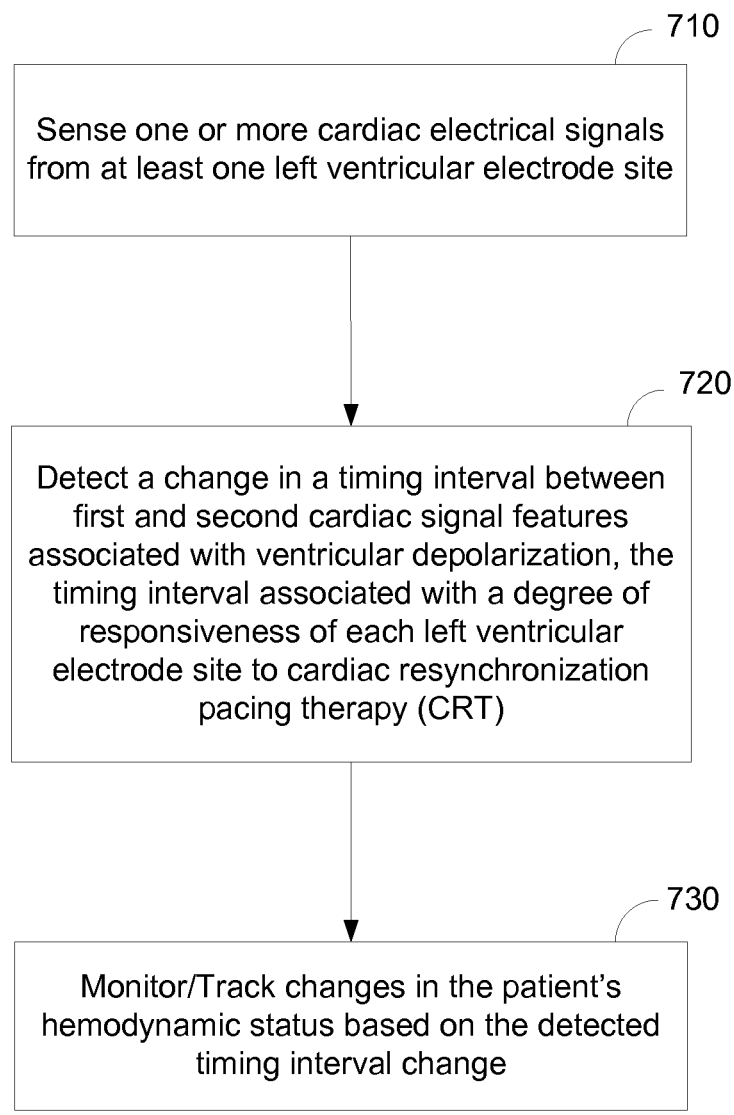
FIG. 5 is a flow diagram illustrating a process for monitoring and/or tracking changes in a patient's hemodynamic status in accordance with embodiments of the invention.

FIG. 5 is a flow graph illustrating a process for monitoring a patient's hemodynamic status in accordance with another embodiment of the present invention. In this illustrative example, changes in a patient's hemodynamic status are detected based on changes in timing intervals associated with ventricular depolarization at a number of left ventricular electrode sites. According to one approach, cardiac electrode signals for a number of left ventricular electrode sites are sensed 710. After the left ventricular cardiac electrode signals are sensed, each from a left ventricular electrode site, a timing interval between first and second cardiac signal features associated with ventricular depolarization is measured for each left ventricular electrode site, where the timing interval is associated with a degree of responsiveness of the left ventricular electrode site to CRT. Changes in the timing interval for each left ventricular electrode site are detected 720, such as by comparing changes in each timing interval relative to a threshold as previously discussed or by detecting a statistically significant change in the timing interval (e.g., change of >20 ms; >20%; >3 sigma standard deviation). Changes in the patient's hemodynamic status may monitored and tracked 730 based on the detected timing interval changes.

Figure 6:
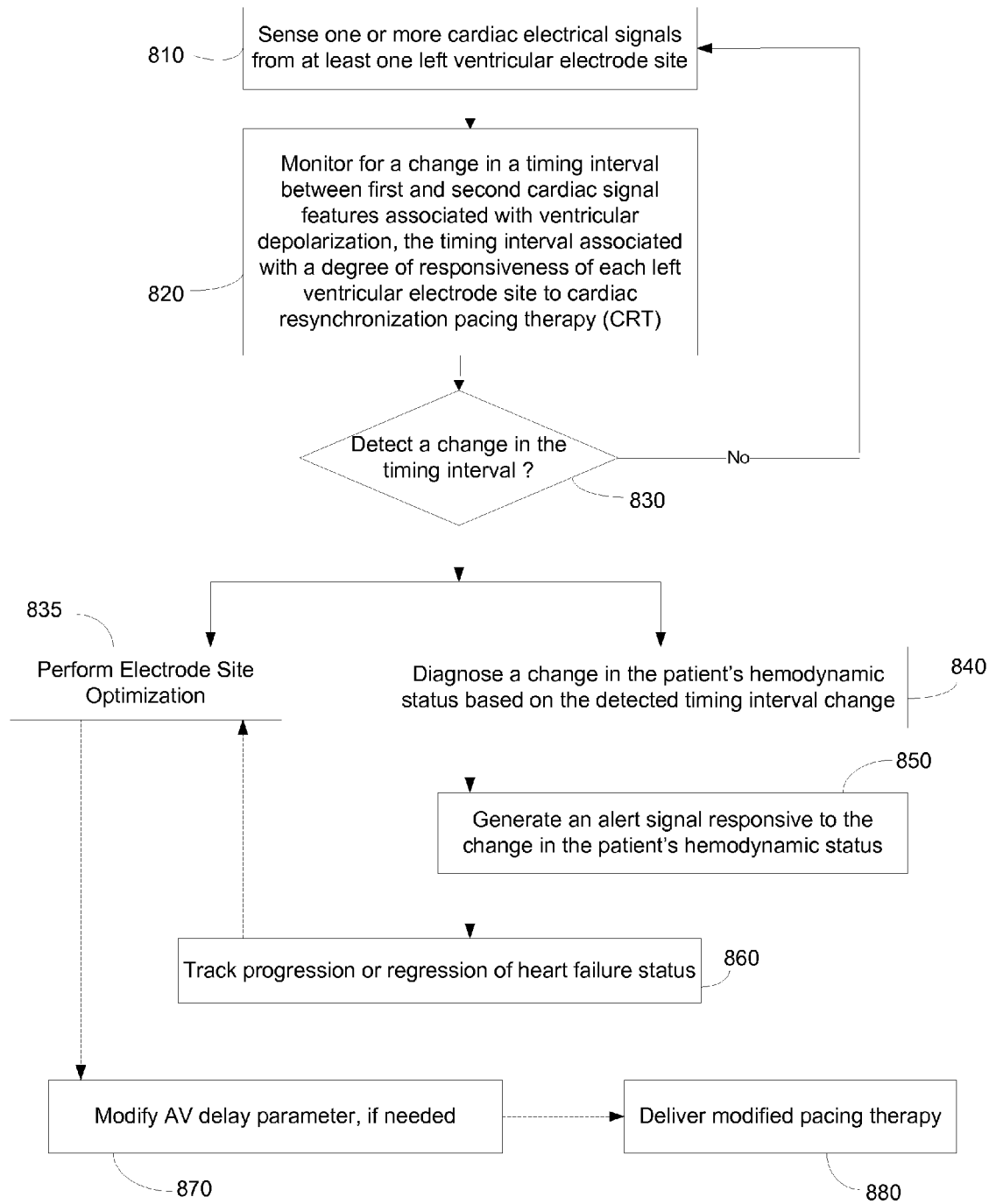
FIG. 6 is a flow diagram illustrating various processes for determining a pacing output configuration and monitoring/tracking changes in a patient's hemodynamic status in accordance with embodiments of the invention.

FIG. 6 is a flow graph illustrating a process for optimizing electrode site selection and monitoring a patient's hemodynamic status in accordance with an embodiment of the present invention. In this illustrative example, cardiac electrode signals for a number of left ventricular electrode sites are sensed 810. After the left ventricular cardiac electrode signals are sensed, each from a left ventricular electrode site, a timing interval between first and second cardiac signal features associated with ventricular depolarization is measured for each left ventricular electrode site, where the timing interval is associated with a degree of responsiveness of the left ventricular electrode site to CRT. Changes in the timing interval for each left ventricular electrode site are monitored 820.

If a change in the timing interval is detected 830, such as by comparing each timing interval to a threshold, one or both of the processes shown in FIG. 6 may be performed, sequentially or in parallel. In response to a detected change in the timing interval, an electrode site optimization procedure may be performed 835 in a manner discussed above. Assuming a different electrode site/vector is selected as one that will provide improved responsiveness to CRT, the AV delay may be modified 870 and the modified pacing therapy delivered 880 in a manner described herein. Electrode site selection optimization and/or AV delay parameter selection may be performed by the therapy device, by a physician via a programmer or APM system, or by any combination of the therapy device, physician, and programmer/APM system.

In response to a detected change in the timing interval, a change in the patient's hemodynamic status may be diagnosed 840 based on the timing interval change. An alert signal may be generated 850 and communicated to a clinician (via a programmer or APM system) in response to the detected timing interval change. The detected timing interval change may be used to track progression or regression of the patient's heart failure status 860. Each of the processes 840, 850, and 860 discussed above may additionally involve the processes of performing electrode site optimization 835 and/or AV delay parameter selection, as is indicated in FIG. 6.

Figure 7:
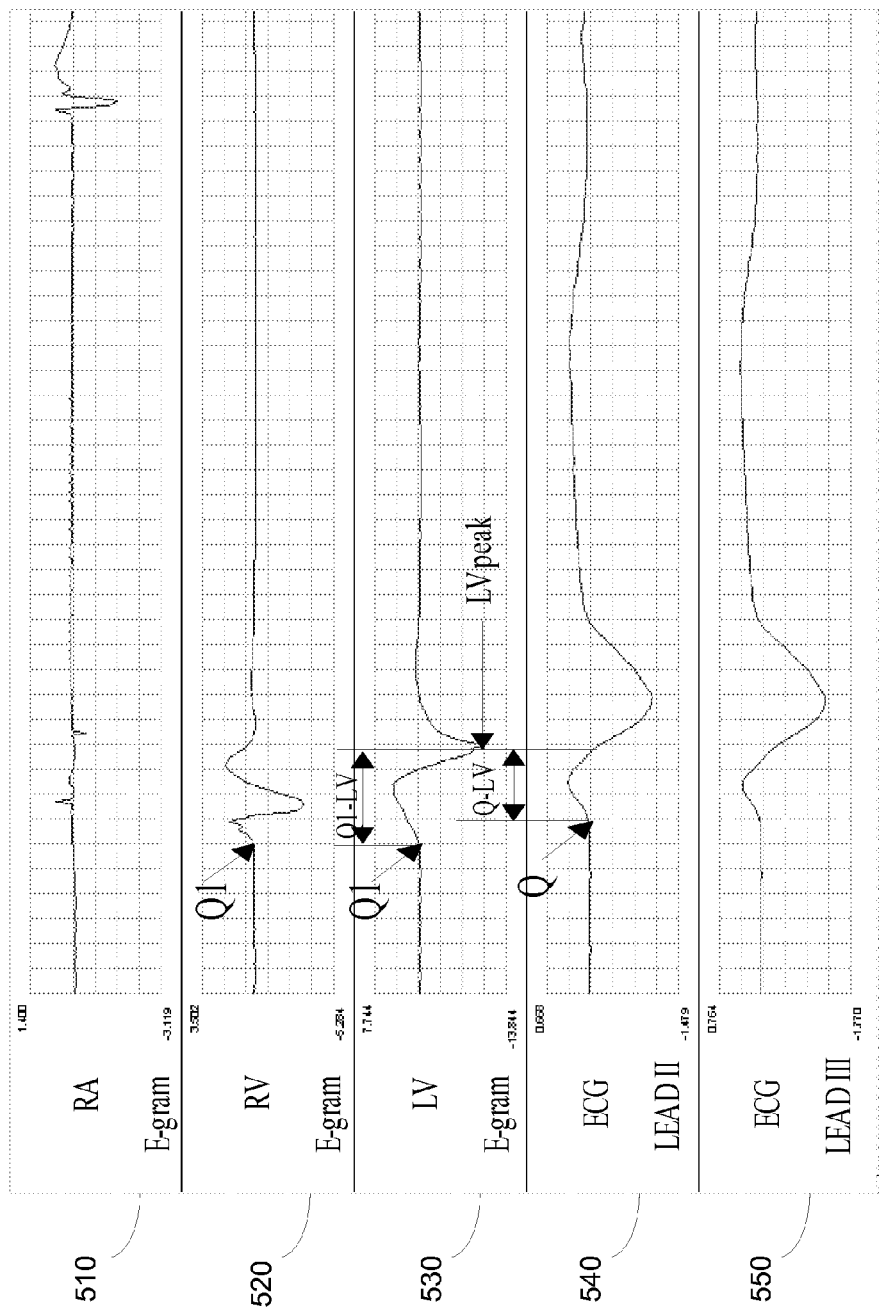
FIG. 7 illustrates is a series of cardiac signal waveforms associated with ventricular depolarization, which includes features useful for determining timing intervals for implementing a pacing output configuration selection methodology in accordance with embodiments of the invention.

FIG. 7 illustrates several electrograms (EGM) and electrocardiograms (ECG) 510-550 for an intrinsic systolic cycle, each measured at a different location. For each EGM and ECG 510-550, a voltage measurement is represented on the vertical axis of each plot. Each signal is taken over time, time being represented on the horizontal axis of each plot.

Each portion of an EGM and ECG is typically given an alphabetic designation corresponding to a pre-determined period of electrical depolarization or excitement. For example, the portion of an electrogram that represents atrial depolarization is commonly referred to as the P-wave (not shown). Similarly, the portion of the electrogram that represents ventricular depolarization is commonly referred to as the QRS complex comprising a Q-wave, an R-wave, and an S-wave. Moreover, the portion of the electrogram that represents ventricular recovery or repolarization is commonly referred to as the T-wave (not shown).

The left ventricle EGM 530 illustrates a maximum deflection peak representing the reflexion on the local electrode of the near field (near the electrode) ventricular activation of the left ventricle labeled LV peak. Also shown in the left ventricle electrogram 530 is the first deflection labeled Q1, corresponding to the onset representing the reflexion on the local electrode of the start of the far field ventricular electrical activation. ECG 540 is a graph for a lead electrode (e.g., far field electrode), which shows the onset of the first deflection of ventricular depolarization that is labeled Q.

Figure 8:
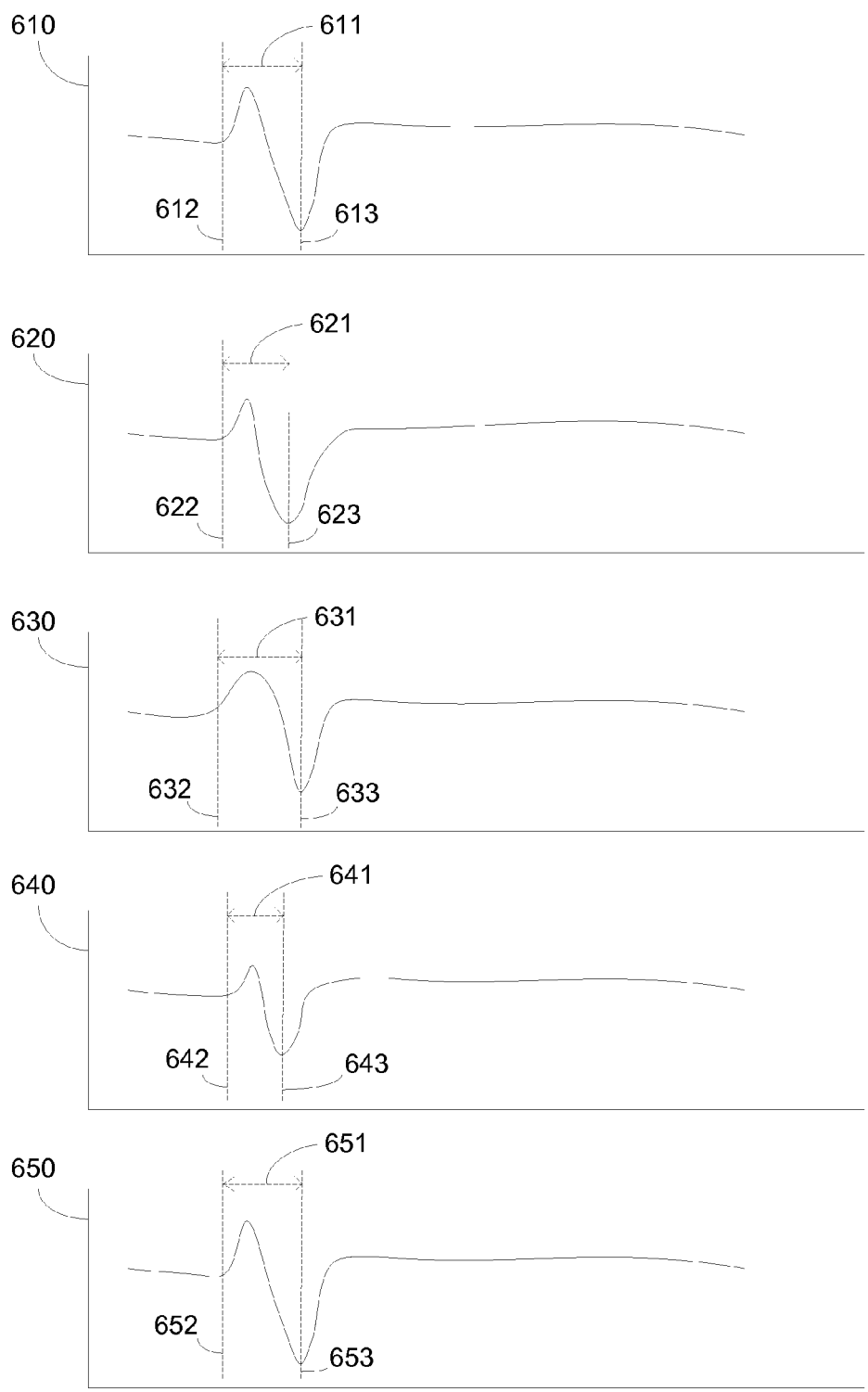
FIG. 8 illustrates cardiac signal waveforms taken from various left ventricular electrode sites and time intervals associated with each site in accordance with embodiments of the invention.

FIG. 8 illustrates cardiac signal waveforms 610-650, each representing a signal taken from a different left ventricular electrode site during intrinsic ventricular depolarization. Each of the waveforms 612-650 is intended to represent a signal received at different electrode sites (or via different sense vectors) during a single ventricular cycle, or they could be from different cycles.

Waveform 610 includes two features, a first deflection 612 and a maximum deflection 613. A time interval 611 is marked between the first deflection 612 and the maximum deflection. Waveforms 620-650 are similarly marked. As FIG. 8 illustrates, each time interval 611, 621, 631, 641 and 651 can be different, even though in some implementations they may all be measured from the same ventricle depolarization cycle. The differences in the timing intervals 611, 621, 631, 641 and 651 may be caused by various abnormalities. As discussed above, in many cases, the effects of CRT on systolic pressure and cardiac output can best be realized by pacing electrode sites with long time intervals. Thus, pacing may be implemented more effectively and/or efficiently by pacing output configurations that take into account the relative responsiveness of each electrode site to CRT.

Time interval 631 of waveform 630 is the longest in duration when compared to the other time intervals 611, 621, 641 and 651 of FIG. 8. In some embodiments, the electrode site corresponding to waveform 630 may be the only electrode site of the left ventricle to receive pacing stimulation because it is associated with the longest time interval. In other embodiments, two or more of the five electrode sites corresponding to waveforms 610-650 may receive pacing stimulation. In such an embodiment, the pacing output configuration, including those electrode sites that receive pacing stimulation and those that do not, may depend on the relative lengths of the timing intervals 611, 621, 631, 641 and 651. A comparison between these timing intervals may be made to determine their relative lengths, as is discussed above.

As was previously discussed, in some implementations, an advanced patient management or APM system may be employed to remotely monitor a patient's responsiveness to CRT and hemodynamic status. If a change in CRT responsiveness or hemodynamic status is detected, for example the APM system may signal the implantable device to initiate an evaluation of its pacing output configuration relative to other configurations that may include alternative electrode sites and/or pacing parameters. In some scenarios, selection of the pacing output configuration may be performed by the implantable device. In other scenarios, the APM system may perform the selection, autonomously or with clinician input. Various therapeutic and/or diagnostic medical devices coupled to the APM system can provide sensing capability for use in detecting the patient's hemodynamic state via a multi-sensor approach. The APM system may be coupled to a variety of patient-external and patient-implantable devices, each device incorporating a set of sensors which are remotely accessible to the APM system.

A user interface may be coupled to the APM allowing a clinician to remotely monitor cardiac functions, as well as other patient conditions. The user interface may be used by the clinician to access information available via the APM. The clinician may also enter information via the user interface for setting up the pacing output configuration functionality. For example, the clinician may select alternate electrode sites or vectors for CRT, particular sensors, hemodynamic status indicators, indicator levels or sensitivities, and/or electromechanical parameters. Methods, structures, and/or techniques described herein may incorporate various APM related methodologies, including features described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Adjusting the AV delay in response to selection of a particular electrode site(s)/vector(s) for optimizing CRT delivery according to the present invention may be accomplished in several ways. According to one approach, the therapy device may vary the AV delay interval used for delivering CRT in an atrial tracking or AV sequential pacing mode in accordance with the sensed or paced atrial rate. Optimal values for the AV delay parameter associated with a particular atrial rate may be computed as linear functions of an intrinsic conduction measurement taken when the particular rate is present. Additional details concerning this approach are described in commonly owned U.S. Pat. No. 7,123,960, which is hereby incorporated herein by reference.

According to another approach, a programmer or APM system may be used to receive a first data value for use in the execution of one or more algorithms. One or more suggested therapy device settings are calculated from the one or more algorithms based on the first data value, and the one or more suggested therapy device settings are displayed on an interactive display screen of the programmer or APM system. In one embodiment, the first data value is a duration interval of a QRS complex. From the duration interval, pacing intervals for an AV delay are suggested based on measured P-R intervals, or pacing intervals for an LV offset are suggested based on a measured duration interval of a V-V-interval between a right ventricular event and a left ventricular event. Additional details concerning this approach are described in commonly owned U.S. Pat. No. 7,181,285, which is hereby incorporated herein by reference. A further approach is described in commonly owned U.S. Pat. No. 6,351,673, which is hereby incorporated herein by reference.

Various modifications and additions can be made to the preferred embodiments discussed hereinabove without departing from the scope of the present invention. For example, as one of ordinary skill in the art will understand, various other embodiments are contemplated within the scope of this disclosure, with various other features, intervals, comparisons, and combinations being used to determine the pacing output configuration. Accordingly, the scope of the present invention should not be limited by the particular embodiments described above, but should be defined only by the claims set forth below and equivalents thereof.

What is claimed is:

1. A method, comprising:
sensing, from within a patient, cardiac electrical signals from a plurality of disparate left ventricular electrode sites;
measuring, for each left ventricular electrode site, a timing interval between first and second cardiac electrical signal features associated with ventricular depolarization, the timing interval comprising a Q1-LV timing interval or a Q-LV timing interval and associated with a degree of responsiveness of the left ventricular electrode sites to cardiac resynchronization pacing therapy (CRT);
detecting a change in the timing interval for each left ventricular electrode site; and
monitoring for a change in hemodynamic status of the patient based on the detected timing interval change.

2. The method of claim 1, wherein monitoring for the change in hemodynamic status comprises tracking progression or regression of a heart failure status.

3. The method of claim 1, further comprising generating an alert signal responsive to the change in the patient's hemodynamic status.

4. The method of claim 1, further comprising modifying selection of one or more of the left ventricular pacing sites responsive to the change in the patient's hemodynamic status.

5. The method of claim 1, further comprising modifying one or more pacing delays responsive to the change in the patient's hemodynamic status.

6. The method of claim 1, further comprising modifying an atrioventricular (AV) delay parameter responsive to the change in the patient's hemodynamic status.

7. The method of claim 1, further comprising modifying delivery of CRT in response to the change in the patient's hemodynamic status.

8. The method of claim 1, wherein detecting the change in the timing interval comprises comparing a change in each timing interval to a predetermined threshold.

9. The method of claim 1, wherein detecting the change in the timing interval comprises comparing a change in each timing interval to a threshold based on a Q1-LV timing interval or a threshold based on a Q-LV timing interval.

10. The method of claim 1, wherein detecting the change in the timing interval comprises comparing a change in each timing interval to one or more thresholds based on sensed intervals for various cardiac electrode sites other than Q1-LV and Q-LV timing intervals.

11. A system, comprising:
a plurality of electrodes positionable at a plurality of disparate sites of the left ventricle and configured for sensing cardiac electrical signals at the disparate left ventricular sites;
a pulse generator coupled to the electrodes and configured to deliver at least a cardiac resynchronization therapy (CRT); and
a processor coupled to the electrodes and the pulse generator, the processor configured to measure, for each left ventricular electrode site, a timing interval between first and second cardiac electrical signal features associated with ventricular depolarization, the timing interval comprising a Q1-LV timing interval or a Q-LV timing interval and associated with a degree of responsiveness of the left ventricular electrode sites to cardiac resynchronization pacing therapy (CRT), the processor further configured to detect a change in the timing interval for each left ventricular electrode site and monitor for a change in hemodynamic status of the patient based on the detected timing interval change.

12. The system of claim 11, wherein the processor is configured to track progression or regression of a heart failure status.

13. The system of claim 11, wherein the processor is configured to generate an alert signal responsive to the change in the patient's hemodynamic status.

14. The system of claim 11, wherein the processor is configured to modify selection of one or more of the left ventricular pacing sites responsive to the change in the patient's hemodynamic status.

15. The system of claim 11, wherein the processor is configured to modify one or more pacing delays responsive to the change in the patient's hemodynamic status.

16. The system of claim 11, wherein the processor is configured to modify an atrioventricular (AV) delay parameter responsive to the change in the patient's hemodynamic status.

17. The system of claim 11, wherein the processor is configured to modify delivery of CRT in response to the change in the patient's hemodynamic status.

18. The system of claim 11, wherein the processor is configured to compare a change in each timing interval to a predetermined threshold.

19. The system of claim 11, wherein the processor is configured to compare a change in each timing interval to a threshold based on a Q1-LV timing interval or a threshold based on a Q-LV timing interval.

20. The system of claim 11, wherein the processor is configured to compare a change in each timing interval to one or more thresholds based on sensed intervals for various cardiac electrode sites other than Q1-LV and Q-LV timing intervals.

* * * * *